United States Patent
Dae et al.

(10) Patent No.: US 6,702,783 B1
(45) Date of Patent: Mar. 9, 2004

(54) ENDOVASCULAR HEAT-AND GAS-EXCHANGE CATHETER DEVICE AND RELATED METHODS

(75) Inventors: Michael W. Dae, Belmont, CA (US); Timothy R. Machold, Moss Beach, CA (US)

(73) Assignee: Radiant Medical, Inc., Redwood City, CA (US)

(*) Notice: Subject to any disclaimer, the term of this patent is extended or adjusted under 35 U.S.C. 154(b) by 2 days.

(21) Appl. No.: 10/068,256

(22) Filed: Feb. 5, 2002

(51) Int. Cl.[7] .................... A61F 7/12; A61M 37/00
(52) U.S. Cl. ..................... 604/113; 604/103.01
(58) Field of Search .............. 604/113, 103.01, 604/509, 26; 607/105

(56) References Cited

U.S. PATENT DOCUMENTS

| | | | |
|---|---|---|---|
| 4,911,689 A | 3/1990 | Hattler | 604/26 |
| 4,986,809 A | 1/1991 | Hattler | 604/26 |
| 5,122,113 A | 6/1992 | Hattler | 604/26 |
| 5,219,326 A * | 6/1993 | Hattler | 604/26 |
| 5,336,164 A * | 8/1994 | Snider et al. | 604/6.14 |
| 5,376,069 A | 12/1994 | Hattler | 604/26 |
| 5,501,663 A | 3/1996 | Hattler et al. | 604/26 |
| 5,865,789 A | 2/1999 | Hattler | 604/26 |
| 6,126,684 A * | 10/2000 | Gobin et al. | 607/113 |

OTHER PUBLICATIONS

Keogh BF, Sim KM, Evans TW, Intravascular Gas Exchange, 1999, FEB, 54(1):38–42.
Hewitt TJ, Hattler BG, Federspiel WJ, A Mathematical Model of Gas Exchange in an Intravenous Membrane Oxygenator, Jan.–Feb. 1998; 26(1):166–78.
Reeder GD, Hattler BG, Rawleigh J, Walters FR, Sawzik PJ, Lund LW, Klain M, Goode JS, Borovetz HS, Current Progress in the Development of an Intravenous Membrane Oxygenator, Jul.–Sep. 1998; 39(3):M461–5.
Shafi AS, Lund LW, Walters FR, Sawzik PJ, Reeder GD, Borovetz HS, Hattler BG, Vibration Analysis of Vessel Wall Motion with Intra Vena Caval Balloon Pumping; Sep.–Jul. 1994; 40(3):M740–2.
Merrill, Ph.D., Tom, Enhancing Endovascular Heat and Mass Transfer,(No Knowledge of Published Date).
Macha M, Federspiel WJ, Lund LW, Sawzik PJ, Litwak P, Walters FR, Reeder GD, Borovetz HS, Hattler BG, Acute in Vivo Studies of the Pittsburgh Intravenous Membrane Oxygentor, Sep.–Oct. 1996; 42(5):M609–15.
Tao W, Schroeder T, Bidai A, Cardenas VJ Jr, Nguyen PD, Bradford DW, Traber DL, Zwischenberger, JB., Improved Gas Exchange Performance of the Intravascular Oxygenator by Active Blood Mixing, Jul.–Sep. 1994; 40(3):M527–32.
Zwischenberger JB, Tao W, Bidani., Intravascular Membrane Oxygenator and Carbon Dioxide Removal Devices: A Review of Performance adn Improvements, Jan.–Feb. 1999; 45(1):41–6.

* cited by examiner

Primary Examiner—Michael J. Hayes
Assistant Examiner—Lina R Kentos
(74) Attorney, Agent, or Firm—Robert D. Buyan; Stout, Uxa, Buyan & Mullins, LLP (57) ABSTRACT

An endovascular catheter device capable of heat and gas exchange with a patient's bloodstream comprises a catheter shaft, a heat exchanger, and a gas exchange element. The heat exchanger and the gas exchange element are in fluid communication with one or more internal lumens of the catheter shaft. The catheter shaft may be connected to a control system that permits a heat exchange fluid to be delivered to the heat exchanger, and that permits a gas to be delivered to the gas exchange element. The catheter device may also comprise one or more flow disruption devices to disrupt the laminar flow of blood around the catheter device. The catheter device may be used to cool and oxygenate a patient's blood, and improve organ function.

79 Claims, 5 Drawing Sheets

ENDOVASCULAR HEAT-AND GAS-EXCHANGE CATHETER DEVICE AND RELATED METHODS

FIELD OF THE INVENTION

This invention relates generally to medical devices and methods of using same. More particularly, the invention relates to devices, systems, and methods for altering a patient's temperature and blood gas concentration levels, such as blood oxygen levels.

BACKGROUND OF THE INVENTION

In many clinical conditions it is desirable to administer oxygen to a patient for the by purpose of increasing the partial pressure of oxygen within the patient's blood. In certain conditions, implantable oxygenators may be employed to administer oxygen directly to a patient's bloodstream. Examples of percutaneous oxygenators include those disclosed in U.S. Pat. Nos. 5,865,789; 5,501,663; 5,376,069; 5,219,326; 5,122,113; 4,986,809; and 4,911,689. The oxygenators disclosed in these references are connected to an inflow conduit that delivers oxygen through a plurality of generally tubular gas-permeable fibers. Oxygen diffuses outwardly through the fibers into the blood while carbon dioxide diffuses inwardly from the blood. A gas outflow conduit then caries any un-diffused oxygen and the carbon dioxide out of the body. At least some of the oxygenators disclosed in these references have attempted to reduce laminar streaming of blood flow around the oxygenators when they are inserted in a patient's vascular system.

Some of these references also disclose warming of the oxygen prior to the delivery of the oxygen to the oxygenator in order to reduce the temperature difference between the patient's blood and the oxygen flowing through the oxygenator. The reduction of the temperature difference acts to reduce condensation that may develop within the oxygenator.

Although the administration of oxygen may provide some benefit in terms of alleviating a patient's symptoms, and helping preserve organ function, the metabolic state of the cells of the patient's organ or organs may be normal or above normal, and thus, the use of oxygen alone to treat patients does not provide completely satisfactory results.

Mild hypothermia has been shown to reduce metabolic requirements of organs, such as the heart and/or the brain. Indeed, if the hypothermia is systemic, the metabolic demands of the entire body are generally reduced, so that the demands placed on the heart may be reduced. Additionally, when the patient's body temperature is reduced and maintained 1° C. or more below normothermic (e.g., less than 36° C. in most individuals), such that the output of the heart increases, the condition and function of the heart muscle may improve significantly due to the combined effects of increased bloodflow to the heart, a temporarily decreased metabolic need and decreased metabolic waste products. Hypothermia may also provide protective effects on a patient's organs by preventing undesirable spread of cellular death or injury.

One method for inducing hypothermia of the heart or entire body is through the use of a heat exchange catheter that is inserted into a blood vessel and used to cool blood flowing through that blood vessel. This method in general is described in U.S. Pat. No. 6,110,168 to Ginsburg, which is expressly incorporated herein by reference. Various heat exchange catheters useable for achieving the endovascular cooling are described in U.S. Pat. No. 5,486,208 (Ginsburg), PCT International Publication WO OO/10494 (Machold et al.), U.S. Pat. No. 6,264,679 (Keller et al.), PCT International Publication WO 01/58397, all of which are expressly incorporated herein by reference.

The potential for shivering is present whenever a patient is cooled below that patient's shivering threshold, which in humans is generally about 35.5° C. When inducing hypothermia below the shivering threshold, it is very important to avoid or limit the shivering response. The avoidance or limiting of the shivering response may be particularly important in patients who suffer from compromised cardiac function and/or metabolic irregularities. An anti-shivering treatment may be administered to prevent or deter shivering. Examples of effective anti-shivering treatments are described in U.S. Pat. No. 6,231,594 (Dae et al.).

Thus, there remains a need in the art for improving patient outcome and organ preservation in patients that suffer from compromised cardiac or respiratory functions.

SUMMARY OF THE INVENTION

The present invention provides a catheter device that is insertable into the vascular system of a human or veterinary patient. The catheter device of the invention generally comprises a) heat exchanger for controlling and adjusting the temperature of a patient, and b) a gas exchange element for delivering gas to the patient via the patient's bloodstream.

An endovascular catheter device may comprise a catheter shaft, a heat exchanger, and a gas exchange element, each connected to the catheter shaft. The catheter shaft may have one or more internal lumens extending along the length of the shaft. The internal lumens are in fluid communication with the heat exchanger and the gas exchange element so that fluid, such as gas or liquid, may flow through the lumens and through the heat exchanger and gas exchange element.

The heat exchanger of the catheter device may be expandable. In certain embodiments of the invention, the heat exchanger may be a heat exchange balloon, and the balloon may comprise a plurality of lobes. The lobes of the balloon may be linearly, helically, or orthogonally disposed around the catheter shaft.

The gas exchange element of the catheter device may comprise a plurality of gas permeable fibers. The gas permeable fibers may be linearly, helically, and/or orthogonally arranged around the catheter shaft. The gas exchange element may be proximally disposed to the heat exchanger. In reference to the disclosure herein, the terms proximal and distal refer to the relative position on the catheter device. In other words, and as understood in the art, proximal refers to a position on the catheter device that would be closer to a physician's hand when the device is being used in practice. Accordingly, distal refers to a position on the catheter device that is relatively farther away from the physician's hand. By way of a specific example, a catheter device in accordance with the invention herein disclosed comprises a heat exchange element that is inserted into a patient's body. Thus, the heat exchange element is distal to the portion of the catheter device that is disposed out of the patient's body.

The foregoing catheter device may also comprise a flow disruption device, such as one or more fins or an expandable or inflatable pulsatile element. The flow disruption device may be connected to the catheter shaft and disposed along the length of the shaft to disrupt the laminar flow of blood around the catheter device as it flows around the gas exchange element or heat exchanger. In embodiments of the invention employing a pulsatile element as a flow disruption device, the pulsatile element may be disposed between the gas permeable fibers and the catheter shaft.

The catheter device may be provided as an element in a system for changing a patient's temperature and/or delivering gas to a patient. The system may include one or more apparatus, which comprise a temperature regulator to deliver a heat exchange fluid to the heat exchanger of the catheter device, and a gas delivery regulator to deliver a gas to the gas exchange element of the catheter device. The control system may also comprise a controller to control the actions of the temperature and gas delivery regulator, a temperature monitoring device, and/or a cardiac monitoring device. The catheter device may also include one or more probes to monitor the patient's temperature, blood gas concentration, and/or cardiac function.

The catheter device of the invention may be used to control a patient's temperature and/or blood gas concentration. In one embodiment, the catheter device may be inserted into a patient's vascular system, a heat exchange fluid may be urged through the heat exchanger, and a gas may be urged through the gas exchange element. The heat exchange fluid may cause a temperature change in the patient's blood. The gas may permeate through one or more gas permeable fibers to be delivered to the blood. The method may also include one or more steps of disrupting the laminar flow of blood to enhance the temperature and gas exchange, and monitoring the patient's temperature, and/or blood gas concentration levels.

The catheter device of the invention may further comprise a system including one or more controllers for automatically controlling the function of the device. The controller may receive a signal from, and be responsive to various sensors, for example, temperature sensors that sense a temperature of the patient and provide a temperature signal to the controller. In response to the sensed temperature, the controller may alter the function of the catheter device to increase or decrease the heat exchanged by the catheter by, for example, altering the temperature of the heat exchange fluid or increasing or decreasing the flow rate of the heat exchange fluid. Similarly, the system may comprise blood gas concentration sensors that provide a signal representing information concerning the blood gas status of the patient, in response to which, the controller may alter the functioning of the gas exchange portion of the catheter by, for example, altering the rate of gas flow, or the composition or concentration of gas flowing through the gas exchange catheter. The sensors may be independently placed on or in the patient, or may be incorporated into the catheter to sense parameters such as blood gases or temperature in the bloodstream.

The method of use of the catheter system may further comprise the step of controlling the thermoregulatory response of the patient. For example, if the temperature of the patient is reduced below the shivering threshold, an anti-shivering mechanism may be employed. Such anti-shivering mechanisms include warming blankets and various drug regimes, as disclosed herein.

Still further aspects and elements of the present invention will become apparent to those skilled in the art upon reading and considering the detailed descriptions of examples set forth herebelow and in the accompanying drawings.

DETAILED DESCRIPTION OF SPECIFIC EMBODIMENTS

The following detailed description is provided for the purpose of describing only certain embodiments or examples of the invention and is not intended to describe all possible embodiments and examples of the invention. For example, although the description herein describes an endovascular catheter device having a heat exchanger and a gas exchange element that are used to cool a patient and provide oxygen to a patient, the catheter device may be used to heat a patient to cause the patient to become normothermic (e.g., ~37° C.) or hyperthermic (e.g., greater than 37° C.), and it may be used to deliver other gases to the patient. In addition, although the catheter device of the invention is illustrated in position proximate to a patient's heart, the catheter device may be used near any organ or organs that may benefit from temperature control or blood gas concentration control. For example, the device may be used in proximity to the brain to cool the brain and provide increased oxygen levels to the brain in order to improve recovery from neurological insults, including stroke and head trauma.

Figure 1:
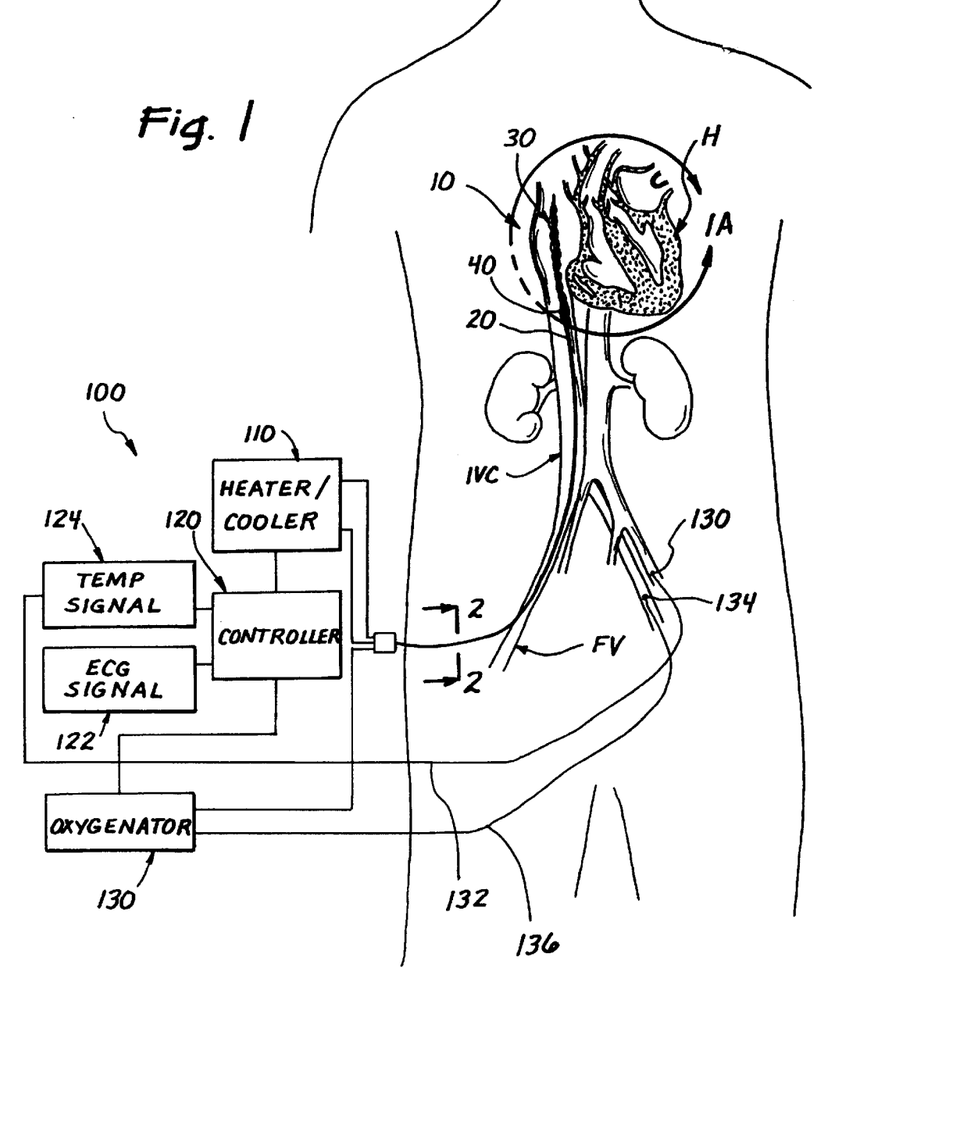
FIG. 1 is a diagram of a human body showing portions of the cardiovascular system including the heart (H), inferior vena cava (IVC) and femoral vein (FV).

Referring to the figures, and in particular, FIG. 1, an endovascular catheter device 10 is positioned in a patient's vascular system. As illustrated, catheter device 10 has been inserted through a person's femoral vein and inferior vena cava so that the distal end of the catheter device is positioned near or in the right atrium of the heart. As described more fully herein, endovascular catheter device 10 comprises a catheter shaft 20; a heat exchanger 30; and a gas exchange element 40. Catheter shaft 20 may be a tube having a proximal end, a distal end, and one or more lumens extending from the proximal end towards the distal end, as described herein. At least one of the lumens of catheter shaft should extend the length of the catheter device. In the embodiment illustrated in FIG. 1, heat exchanger 30 is positioned at the distal end of the catheter device, and gas exchange element 40 is proximal to heat exchanger 30.

Catheter device 10 may be connected to a control system 100. Control system 100 may be one apparatus, or a plurality of apparatus. As illustrated, control system 100 comprises a temperature regulator 110 to control the delivery and return of heat exchange fluid, and a gas delivery regulator 130 to control the delivery and return of gases, as described herein. Control system 100 may also comprise a controller 120 for controlling the flow of heat exchange fluid through temperature regulator 110, and for controlling the flow of gas through gas delivery regulator 130. Controller 120 may also be operably connected to an electrocardiogram (ECG) monitoring apparatus, and/or to a temperature monitoring apparatus. The ECG monitoring apparatus may provide an ECG signal 122 to controller 120, and the temperature monitoring apparatus 124 may provide a temperature signal 124 to controller 120.

Various sensors may be placed on or in the patient to sense various parameters of the patient and generate a signal that is carried to the controller to allow the controller to control the function of the catheter device based on those parameters. For example, a temperature sensor 130 may be placed in the patient, for example in the femoral vein contra-lateral to the location of the catheter device, to sense the core temperature of the patient and provide temperature information of the patient by a connection 132 to the controller. In response to this information, the controller may alter the temperature of the heat exchange fluid to increase the patient's temperature, decrease the patient's temperature, or maintain the patient's temperature. In addition, or alternatively, the controller may alter the flow rate of the heat exchange fluid to cause an increase or decrease of the patient's blood temperature. Likewise, a blood oxygen sensor 134 may provide blood gas information by connection to the controller 136 that would cause the controller to increase the oxygen flow, decrease the oxygen flow, increase or decrease the pressure, or the like. In addition, it may be possible to control the gas concentration of the gas flowing through the gas exchange element depending on the gas concentration measured in the blood by sensor 134.

Figure 1A:
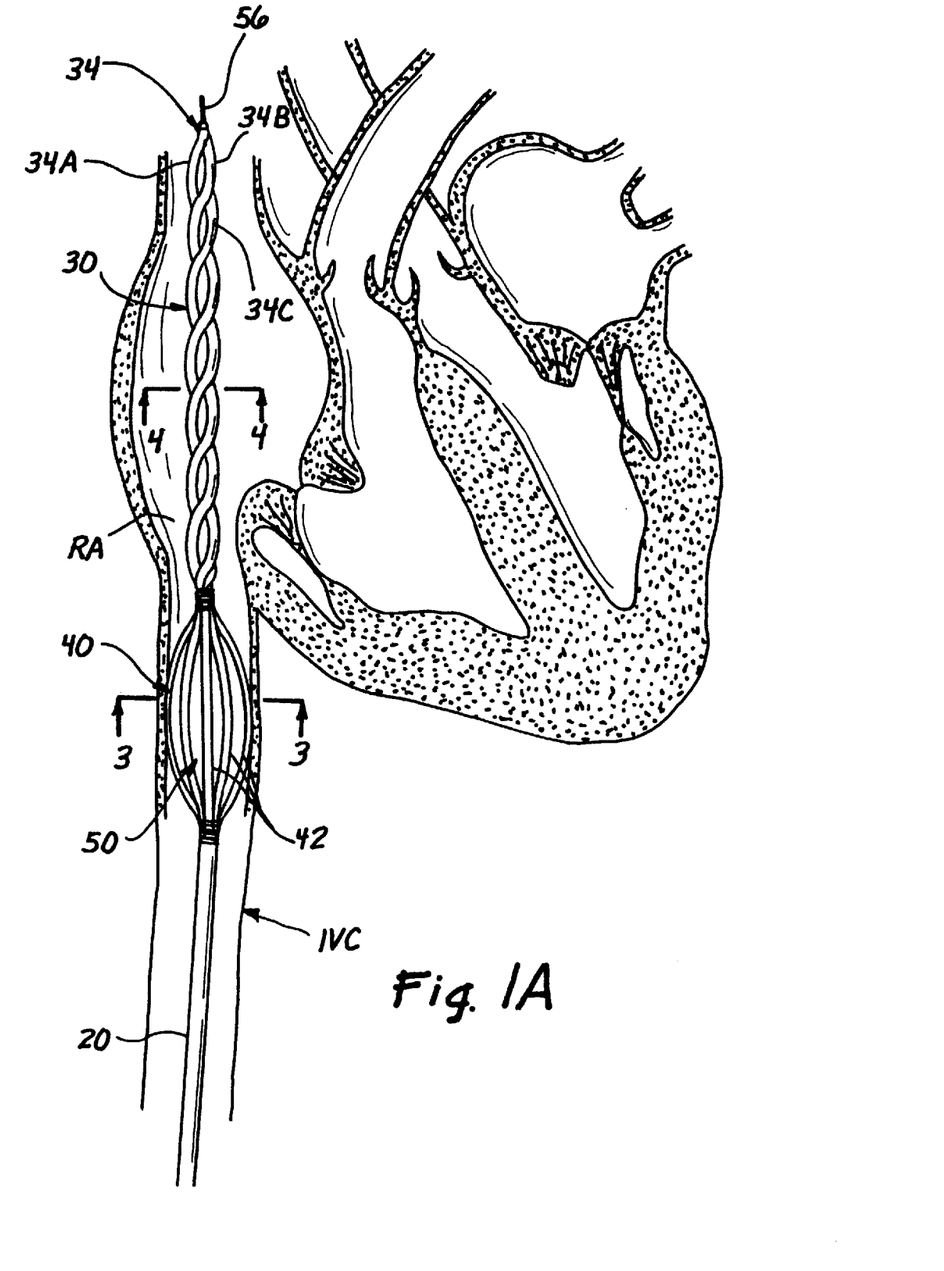
FIG. 1A is a cut-away view of the heart (H) and great vessels, showing the inferior vena cava (IVC), superior vena cava (SVC), and right atrium (RA) with a catheter device positioned in the IVC, RA, and SVC.

FIG. 1A is a magnified view of the distal portion of catheter device 10 illustrated in FIG. 1. As depicted in FIG. 1A, heat exchanger 30 comprises a plurality of outer heat exchange lumens 34. In the illustrated embodiment, heat exchanger 30 comprises three heat exchange lumens 34A, 34B, and 34C helically arranged about an inner lumen 32 (see FIG. 4). In other embodiments, heat exchange lumens 34A, 34B, and 34C could be arranged linearly, e.g., the lumens may be disposed around inner lumen 32 and parallel to the length of catheter shaft 20, or heat exchange lumens could be arranged around inner lumen 32 and orthogonal to the length of the shaft. In other embodiments, heat exchanger 30 may comprise a single outer lumen. The lumens 34 may be made of any suitable material that is flexible and elastic, and that provides sufficient heat transfer properties to cause changes in the temperature of a patient's bloodstream. One example of a suitable lumen material includes polyethylene terephthalate (PET). Guide wire 56 is shown extending from the distal end of heat exchanger 30. Guide wire 56 provides support to the catheter device as it is inserted into a patient's vascular system.

Heat exchanger 30 of the catheter device of the invention may be expandable such that the outer lumen or lumens 34 may be expanded and contracted. The expandable nature of the heat exchanger 30 facilitates insertion of the catheter device 10 into a patient's vascular system, and improves the heat exchange capabilities of the catheter device. For example, contracting the heat exchanger reduces the cross-sectional size of the heat exchanger so that it can be inserted into a vein or the like without risking damaging the vein, or the catheter device. In addition, expanding the heat exchanger will increase the surface area of the heat exchanger so that more blood is exposed to the heat exchange surface and the temperature of the blood may be efficiently controlled. In one embodiment of the invention, the outer lumen or lumens 34 may be one or more balloons, for example a multi-lobed balloon. Examples of endovascular heat exchangers include those disclosed in PCT publications WO 01/13809 and WO 01/58397, the contents of which are hereby incorporated by reference.

As shown in FIG. 1A, a gas exchange element 40 is proximally disposed with respect to heat exchanger 30. Gas exchange element 40 is provided to deliver gas to a patient by exposing the blood circulating around the catheter device 10 to the gas flowing through the gas exchange element 40. In certain embodiments of the invention, the gas may be oxygen. In other embodiments of the invention, the gas may be an anesthetic. Gas exchange element 40 may also permit gas to be removed from the patient's blood. For example, one gas exchange element may permit the delivery of oxygen to the patient's blood, and the removal of carbon dioxide from the patient's blood. In the illustrated embodiment of the invention, gas exchange element 40 comprises one or more gas permeable fibers 42 disposed around catheter shaft 20. The gas permeable fibers 42 may be linearly arranged so that the length of the fibers is generally parallel to the length of the catheter shaft 20. Gas permeable fibers 42 may also be helically and/or orthogonally arranged around catheter shaft 20. In embodiments of the invention where gas exchange element 40 is distally disposed with respect to heat exchange element, gas permeable fibers 42 may be arranged around a lumen extending through gas exchange element 40. Gas permeable fibers 42 may be made of any suitable material that is flexible and permits the transfer of gas across the fiber, including, but not limited to polypropylene or a composite that comprises a microporous polyethylene outer layer, a polyurethane intermediate layer, and a microporous polyethylene inner layer. Polypropylene fibers may be coated with a gas permeable membrane, such as silicone rubber. Some specific examples include the publicly available Mitsubishi KPF190M and MHF200L fibers. Examples of gas exchange elements are disclosed in U.S. Pat. No. 5,865,789; 5,501,663; 5,376,069; 5,219,326; 5,122,113; 4,986,809; and 4,911,689, the contents of all of which are incorporated herein by reference.

Heat exchanger 30 is illustrated in FIG. 1A being positioned in a patient's right atrium, and gas exchange element 40 is illustrated in the patient's inferior vena cava. Thus, as blood flows through the inferior vena cava towards the patient's heart, it will receive gas from gas exchange element 40, and then it may experience a temperature change as it flows around heat exchanger 30. In addition, blood flowing through the superior vena cava towards the heart will similarly be subject to a temperature change as it flows around heat exchanger 30. Thus, blood entering the right ventricle will have been exposed to gas and a temperature change prior to entering the right ventricle. In one embodiment, the catheter device 10 may be used to cool the blood and deliver oxygen to the blood. Accordingly, blood flowing into the right ventricle will have been oxygenated as it flows around gas exchange element 40, and may be cooled as it flows around heat exchanger 30.

Catheter device 10 may also comprise one or more flow disruption devices 50 to disrupt the laminar blood flow around the catheter device. As understood by persons skilled in the art, blood may flow around the catheter device and may become laminarly organized so that certain streams or lamina will contact the catheter device, but other lamina will not. Thus, disrupting the laminar flow of blood around the catheter device increases the probability that more blood will be exposed to the catheter device. Any type of flow disruption device may be used in accordance with the present invention. For example, one or more ribs may be provided on the exterior of the catheter shaft, the gas exchange element, or the heat exchanger. In the illustrated embodiments of the invention, the flow disruption device 50 comprises a pulsatile element 52. For example, the pulsatile element 52 may be a balloon. Pulsations of the balloon may disrupt laminarity of blood flowing around the catheter device 10 to increase the exposure of the blood to the gas exchange element 40 and heat exchanger 30 of the catheter device 10. In certain embodiments of the invention, flow disruption devices 50 are provided on the catheter device upstream of the gas exchange element 40 and/or upstream of the heat exchanger 30. Thus, blood will flow around the catheter device 10 and will flow around the flow disruption device 50 before flowing around the gas exchange element 40 and/or heat exchanger 30. In the embodiment illustrated in FIGS. 1A, 5C, 5D, 5E, and 5F, the flow disruption device is proximal to the heat exchange element. In the embodiment illustrated in FIGS. 5A and 5B, the flow disruption device is distal to the heat exchange element.

In the illustrated embodiment of the invention, the flow disruption device 50 comprises a pulsatile balloon. In one embodiment, the pulsatile balloon is disposed around the guide wire lumen 46 of the catheter sheath 20 beneath the gas permeable fibers 42 (see FIG. 3). Accordingly, the pulsatile balloon may be provided as an element of gas exchange element 40. In this embodiment, the pulsatile balloon will inflate and deflate within gas exchange element 40 and will disrupt laminar blood flow around the gas permeable fibers 42 of gas exchange element 40 and may increase the rate of gas exchange through the fibers. In other embodiments of the invention, the pulsatile balloon may be provided as an element of the catheter device separate from the gas exchange element. For example, the gas exchange element may be positioned adjacent to the heat exchanger. In other words, gas exchange element 40 may be positioned in proximity to the heat exchanger 30 to enhance gas exchange and/or to increase the affinity of hemoglobin for oxygen in blood flowing around the gas exchange element. For example, if the gas exchange element 40 is positioned upstream of the heat exchanger 30, relatively warmer blood will flow across the gas exchange element 40 and gas exchange (e.g., oxygen/carbon-dioxide exchange) may be enhanced. In addition, the oxygenated blood will then become cooled, and the affinity of hemoglobin for oxygen will increase due to the temperature decrease in the blood. Or, if gas exchange element 40 is positioned downstream of the heat exchanger 30 that is cooling blood, relatively colder blood will flow around gas exchange element 40, and the affinity of hemoglobin for oxygen may be to increased before oxygenation. Thus, the pulsatile balloon may be provided proximal to the gas exchange element 40 and proximal to the heat exchanger 30 (FIG. 5C); the pulsatile balloon may also be provided proximal to the gas exchange element 40 and distal to the heat exchanger 30 (FIG. 5B); or the pulsatile balloon may be provided distal to the gas exchange element 40 and distal to the heat exchange element 30 (not shown). In addition, a plurality of pulsatile balloons and/or gas exchange elements may be provided on the catheter device of the invention, for example, a first pulsatile balloon may be provided as an element of gas exchange element 40, as described above, and a second pulsatile balloon may be provided as a separate element.

Figures 2, 3, 4, 6:
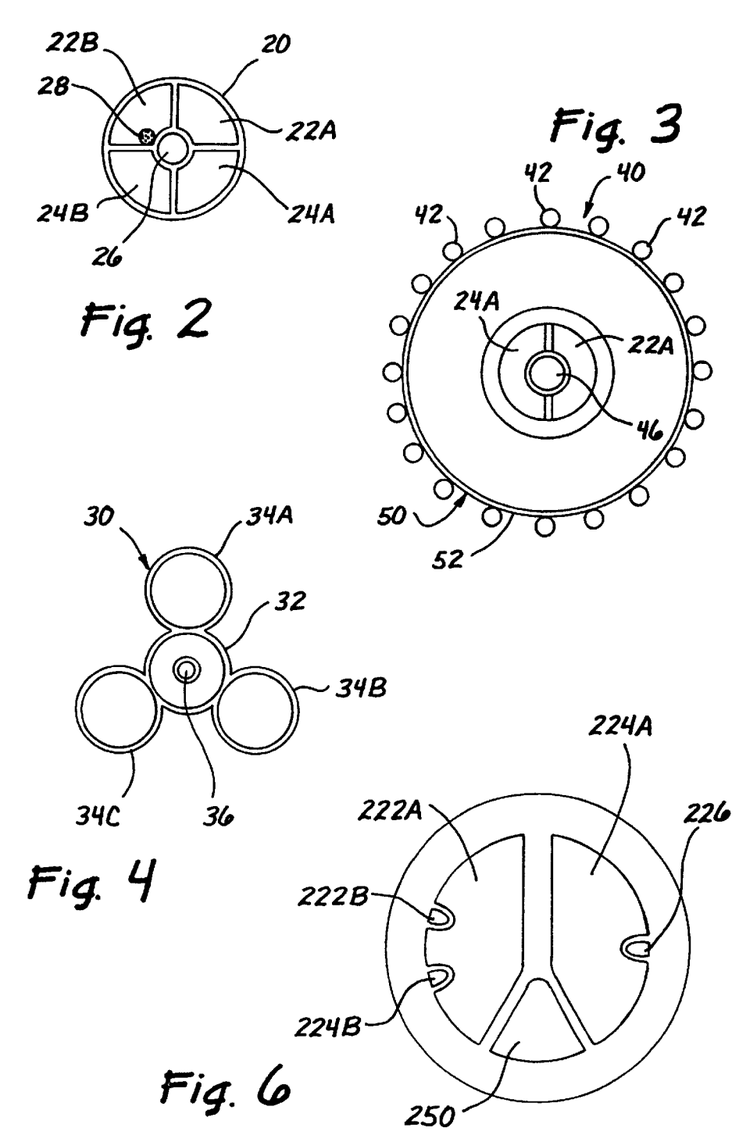
FIG. 2 is a sectional view along line 2—2 of FIG. 1.
FIG. 3 is a sectional view along line 3—3 of FIG. 1A.
FIG. 4 is a sectional view along line 4—4 of FIG. 1A.
FIG. 6 is a sectional view similar to FIG. 2, but depicting another configuration of the catheter device.

FIG. 2 is a sectional view along line 2—2 of FIG. 1. FIG. 2 depicts a sectional view of catheter shaft 20 of catheter device 10. Catheter shaft 20 comprises a plurality of internal lumens permitting the flow of fluid, such as a gas or liquid, through the lumens to and from the heat exchanger 30 and gas exchange element 40. In the illustrated embodiment, catheter shaft 20 comprises a heat exchange fluid inflow lumen 22A, a heat exchange fluid outflow lumen 24A, a gas inflow lumen 22B, a gas outflow lumen 24B, and a guide wire lumen 26. As shown in FIG. 2, all the internal lumens in the shaft are essentially the same size, but that is just for simplification and for purposes of illustration. As one of skill in the art would recognize, depending on the configuration of the gas exchange region and the heat exchange region, various configurations of the shaft might be appropriate. For example, the lumens for the input and outflow of the gas might be significantly smaller than the lumens for the input and outflow of the fluid, the lumen for the guide wire might not be centrally located. In addition, the individual lumens may be disposed at different locations within the catheter shaft. One example of a shaft cross section that gives examples of a variation that is contemplated is shown in FIG. 6. In FIG. 6, the guide wire lumen 226 is extruded along one wall of the shaft. Two small lumens 222B, 224B are extruded for inflow and outflow lumens respectively for the gas to be exchanged in the gas exchange element 40. An inflow lumen 222A for the heat exchange liquid such as saline is provided as is an outflow lumen 224A. An additional lumen 250 is provided and is fluidly connected to the pulsatile balloon 50 for providing a pulsing fluid to, for example, inflate and pulse the pulsatile balloon. Catheter shaft 20 may also include a control wire 28 extending along the length of catheter shaft 20. Control wire 28 may provide means for monitoring a patient's temperature, heart rate, blood gas concentration, etc. Accordingly, control wire 28 may be a temperature probe, an ECG probe, a gas probe, or any combination thereof. As discussed elsewhere herein, such probes or sensors may additionally or alternatively be provided as separate elements from the catheter device.

Catheter shaft 20 may be operably connected to an apparatus having a temperature ray regulator 110 and gas delivery regulator 130 so that the inflow lumens 22A and 22B of catheter shaft 20 may receive fluid, such as liquid or gas, from the apparatus and deliver the fluid to heat exchanger 30 or gas exchange element 40. In reference to the gas exchange element 40, fluid, such as gas or liquid, may flow from gas delivery regulator 130 through gas inflow lumen 22B to gas exchange element 40. In one embodiment, the fluid will flow towards the distal end of gas exchange element 40 where it will then be diverted into one or more gas permeable fibers 42. Accordingly, the flow of fluid through gas permeable fibers 42 is in an opposite direction from the flow of blood over catheter device. Once the fluid flows through gas permeable fibers 42, the fluid may converge into gas outflow lumen 24B and be vented at the gas delivery regulator 130. Thus, the lumens of catheter shaft 20 and gas exchange element 40 are in fluid communication with each other.

Similarly, heat exchanger 30 may be in fluid communication with the lumens of the catheter shaft. For example, heat exchange fluid may flow from temperature regulator 110 through heat exchange fluid inflow lumen 22A towards the distal end of heat exchanger 30. Heat exchange fluid may then be diverted into one or more outer lumens 34, and then flow against the direction of blood flow and converge into heat exchange fluid outflow lumen 24A of catheter shaft 20 where it may then flow back to temperature regulator 110 for repeated circulation. One example of a heat exchange fluid is saline; however, other fluids may also be used in accordance with the invention. In other embodiments of the invention, the heat exchanger may comprise a thermoelectric element or a chemically cooled member mounted within or on the catheter body and operably connected to control system 100.

FIG. 3 is a sectional view along line 3—3 of FIG. 1. FIG. 3 illustrates one embodiment of catheter device 10 in which pulsatile balloon 50 is disposed between guide wire lumen 46 and gas permeable fibers 42 of gas exchange element 40. Pulsatile balloon 50 is shown in an inflated state in FIG. 3 such that the outer wall of pulsatile balloon 50 is abutting gas permeable fibers 42. In reference to FIG. 3, guide wire lumen 46 will be understood to be the same as guide wire lumen 26 of FIG. 2 except that it has been numbered to correspond with the numbering of gas exchange element 40.

Pulsatile balloon 50 is similarly controlled as gas exchange element 40 and heat exchanger 30. In that regard, a lumen may be provided in catheter shaft 20 that extends to pulsatile balloon 50. A fluid may then be urged from the control system 100 to inflate and deflate the balloon. For example, a fluid, such as a gas or liquid, may be directed under pressure from the controller through a lumen to the pulsatile balloon. Subsequently, the fluid may be withdrawn, or directed, away from the balloon. This may be provided by repeatedly increasing and decreasing the pressure of the fluid passing to the balloon. Or, the pulsatile action may be provided by directing the fluid with positive pressure into the balloon, and allowing the fluid to be vented away from the balloon. To improve the laminar disruption of blood flow, the increase and decrease of fluid pressure should be repeated periodically. For example, the pulsation should occur at a frequency that sufficiently disrupts the laminar blood flow to maximize the heat and gas exchange with the catheter device. Because the flow rate of blood through any particular vessel may vary depending on, among other things, vessel diameter, the flow rate should be determined by the attending physician. This determination may be facilitated by the sensors disclosed herein that monitor the patient's temperature, blood gas concentration, etc. Examples of suitable gases for inflating pulsatile balloon 50 include helium or carbon dioxide; however, other gases may be used. Other means of pulsing the pulsatile balloon may also be employed. For example, that balloon may be in series with the heat exchange balloon, and the heat exchange fluid may be supplied in a pulsatile fashion, causing the pulsatile balloon to pulse. This is particularly the case if the pulsatile balloon is slightly elastomeric while the heat exchange balloon is essentially non-compliant. Likewise, the pulsatile element may be in series with the gas exchange element and the gas supplied to the gas exchange element may be supplied at pulsing pressures. These and other similar means may be employed to cause the pulsatile element, for example a balloon to pulse and to therefore break up laminar flow. The pulsation of pulsatile balloon may be controlled to achieve a desired pulsation rate to optimize the exchange of heat or gas between the blood and the catheter device of the invention. In one particular example, the pulsation may occur between 10 and 60 times per minute (e.g., about 0.17 Hz to about 1 Hz).

FIG. 4 is a sectional view along line 4—4 of FIG. 1. FIG. 4 illustrates one embodiment of catheter device 10 in which heat exchanger 30 comprises a tri-lobed 34A, 34B, 34C heat-exchange balloon. Lobes 34A, 34B, and 34C are helically arranged around an internal lumen 32, which includes guide wire lumen 36 extending therethrough. Similar to FIG. 3, guide wire lumen 36 will be understood to be the same guide wire lumen 26 (FIG. 2) and 46 (FIG. 3) except that it has been numbered to correspond with the numbering of heat exchanger 30. In accordance with the foregoing description, heat exchange fluid may be passed distally through internal lumen 32 and proximally through lobes 34A, 34B, and 34C.

Figure 5A:
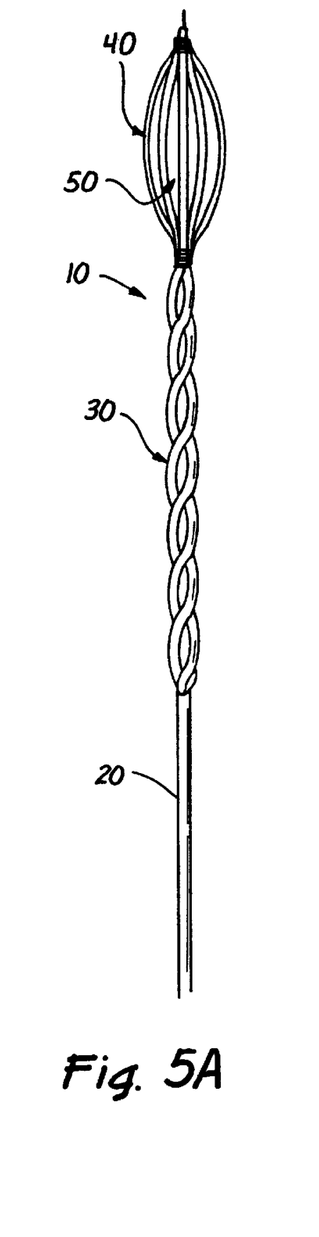
FIG. 5A is a schematic of a catheter device having a gas exchange element disposed distal to the heat exchanger.

FIGS. 5A–5E illustrate various other embodiments of the invention. FIG. 5A illustrates a catheter device 10 that comprises a catheter shaft 20, a heat exchanger 30, and a gas exchange element 40. Gas exchange element 40 includes a pulsatile balloon disposed between a guide wire lumen (not shown) and the gas permeable fibers. In this embodiment, gas exchange element 40 is positioned distal to the heat exchange element. This embodiment of the catheter device may be useful when the gas exchange element is positioned upstream of the heat exchange element. For example, if this embodiment of the catheter device were positioned in the superior vena cava, as illustrated in FIG. 1A, blood flowing from the superior vena cava into the right atrium could be oxygenated prior to being cooled. In addition, the embodiment of the catheter device illustrated in FIG. 5A may be useful where it is desired to cool the blood prior to oxygenation. For example, condensation may develop in the gas permeable fibers because the blood is typically warmer than the oxygen flowing through the gas permeable fibers. The condensation may cause the fibers to become clogged, and decrease their ability to allow gas to permeate therethrough. Thus, with the embodiment shown in FIG. 5A, the blood could be cooled to reduce the temperature difference between the blood and the oxygen flowing through the gas permeable fibers so that condensation formation in the fibers is reduced. It will also be appreciated that the gas may be warmed before introduction into the system, or it may be dried to prevent condensation.

Figure 5B:
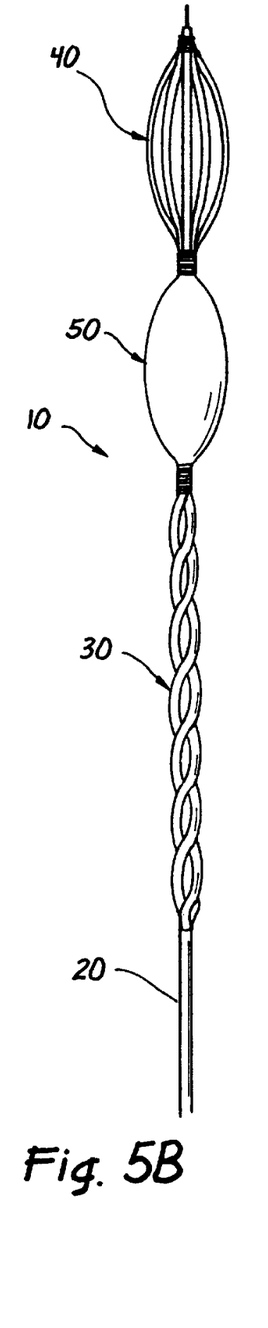
FIG. 5B is a schematic of a catheter device having a gas exchange element at its distal end and a pulsatile balloon disposed proximal to the gas exchange element, and a heat exchanger proximal to the pulsatile balloon.

FIG. 5B illustrates another embodiment of the invention in which catheter device 10 comprises a catheter shaft 20, a heat exchanger 30, a pulsatile balloon 50, and a gas exchange element 40. In this embodiment, gas exchange element is distal to pulsatile balloon 50, and pulsatile balloon 50 is distal to heat exchanger 40. Depending on the direction of blood flow, pulsatile balloon 50 may cause the blood flow to be disrupted before the blood flows around the gas exchange element or around the heat exchanger.

Figure 5C:
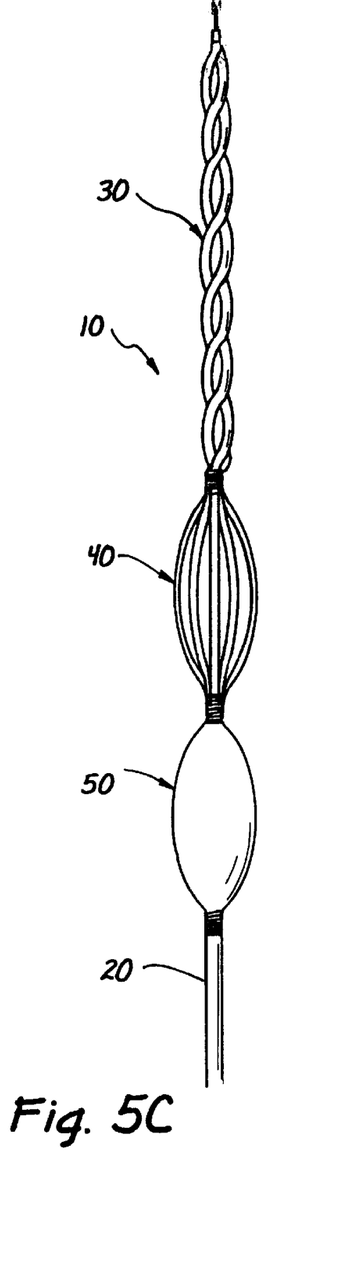
FIG. 5C is a schematic of a catheter device having a heat exchanger at its distal end and a gas exchange element disposed proximal to the heat exchanger, and a pulsatile balloon disposed proximal to the gas exchange element.

FIG. 5C depicts yet another embodiment of the invention. In this embodiment, pulsatile balloon 50 is proximal to gas exchange element 40, which is proximal to heat exchanger 50.

Figure 5D:
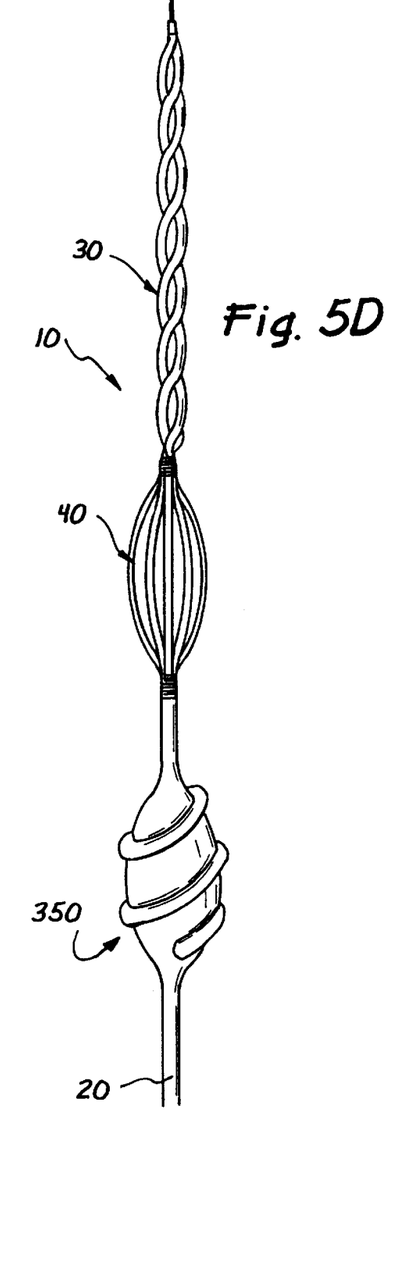
FIG. 5D is a schematic of a catheter device having a flow disruption device proximally disposed to the gas exchange element.
Figure 5E:
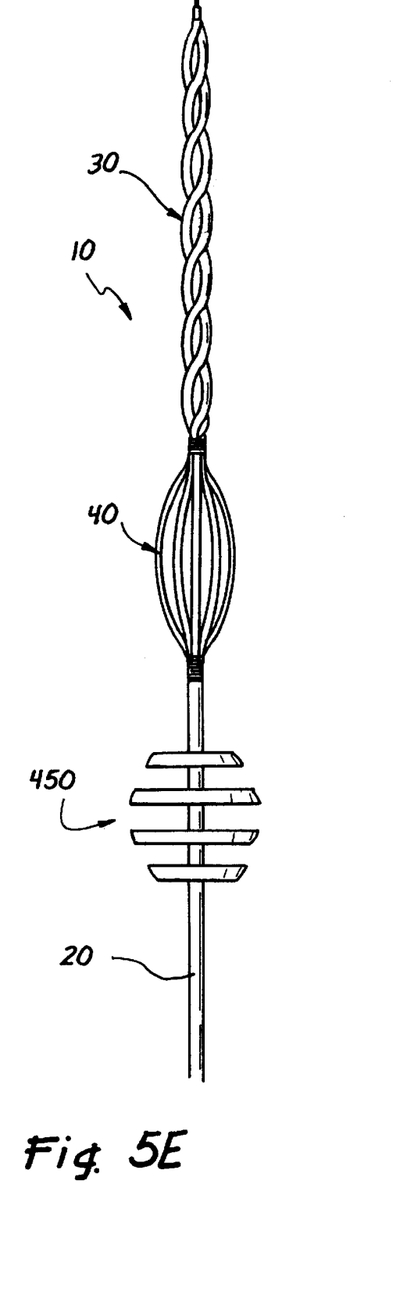
FIG. 5E is a schematic of a catheter device having another flow disruption device proximally located to the gas exchange element.

As indicated elsewhere herein, flow disrupters other than pulsatile balloons may be useful to break up laminar flow and enhance heat or gas transfer between the blood and the catheter device. For example, as shown in FIG. 5D, a rigid, or somewhat rigid, fin like structure 350 on the catheter shaft proximal of the gas exchange element and the heat exchange balloon may act to disrupt the laminarity of the blood flow. If the fin-like structure is collapsible, that may enhance insertion into the blood vessel. Once in the vessel, the fins may become outwardly biased to unfold into the bloodstream. Alternatively, they may be shaped so that the blood flow unfurls them into a shape that will disrupt laminar flow.

The invention may include an inflatable element that, when inflated has a shape that disrupts laminar flow along the catheter shaft. For example, in FIG. 5E a series of inflatable discs 450 form a structure that disrupts blood flow as it flows from the proximal end toward the distal end along the catheter and by breaking up the laminarity of flow, enhances the gas and heat exchange at the gas exchange element and the heat exchange balloon. It will be appreciated that any number of different shapes may be employed for this purpose, and that the shaped inflatable elements may also be pulsed to further enhance their effectiveness.

The catheter device of the present invention may be used to control either a patient's temperature, a patient's blood gas concentration, or a combination of both. In one example, the catheter device may be used to cool and oxygenate a patient's blood. Such a use may be particularly beneficial for patients who have suffered from a myocardial infarction or stroke. The catheter device of the invention may be inserted into a patient's vascular system. The catheter device is advanced within the patient so that the heat exchanger and gas exchange elements are in proximity to an organ that may benefit from cooling or oxygenation, for example a heart. The position of the catheter device may be monitored during the procedure by monitoring the position of the guide wire using conventional means. When the catheter device is in a desired position, heat exchange fluid may be directed or urged through the heat exchanger to cause a temperature change in the patient's blood. Similarly, gas may be directed or urged through the gas exchange element so that the gas may permeate through the gas exchange element into the patient's blood. Thus, the catheter device may be used to control the patient's temperature and/or gas concentration.

The foregoing method may also be practiced by disrupting the laminar flow of blood around the catheter device to enhance the temperature and gas exchange between the catheter device and the blood. For example, the laminar flow of blood may be disrupted by the pulsation of one or more pulsatile balloons positioned adjacent the heat exchanger or gas exchange element. In addition, the method may include one or more steps of monitoring the patient's temperature and/or blood gas concentration. The monitoring step may be performed by utilizing one or more probes disposed within or on the catheter device (not shown), or separately located on the patient as shown in FIG. 1.

In addition, the methods of the invention may include one or more steps of administering cellular protective agents, such as agents that reduce or prevent, cellular death (apoptosis) resulting from injury. Protective agents may include, but are not limited to, anti-excitotoxic agents, such as glutamate receptor modulators, gamma-aminobutyric acid (GABA) receptor modulators, ion channel modulators, such as calcium channel blockers, and free radical scavengers.

The cooling of the patient's body may cause some shivering to occur, if the patient's core body temperature is cooled to less than about 35.5° C. In such cases, it may be desirable to administer an anti-shivering mechanism to prevent or lessen the shivering and enhance the patient's comfort. An anti-shivering mechanism may comprise the application of warmth to the patient's skin as may be accomplished by a warming blanket of the type commonly used in hospitals. Alternatively or additionally, an anti-shivering mechanism may comprise the administration of drugs or agents to minimize or prevent the shivering response. Examples of agents that are useable for this purpose are described in U.S. Pat. No. 6,231,594 (Dae et al.), which is incorporated herein by reference. For example, an anti-shivering mechanism may comprise the steps of:

(i) warming the skin;
(ii) administering an initial bolus dose of a first anti-thermoregulatory response agent to the patient (for example an oral dose of a serotonin 5 HT1a receptor agonist such as 60 mg of buspirone);
(iii) administering a subsequent dose of a second anti-thermoregulatory response agent to the patient (for example an initial intravenous dose of an opioid receptor agonist such as 50 mg of meperidine administered by slow push followed by a similar second dose); and
(iv) administering a further dose of the second anti-thermoregulatory response agent by constant IV administration (for example, constant IV administration of about 25 mg/hr of meperidine).

Alternatively, another anti-shivering treatment that may be more suitable for longer term use (e.g., more than 24 hours) comprises the following steps:

(i) administering a first dose of an anti-thermoregulatory response agent to the patient (for example an intravenous dose of an opioid receptor agonist such as 50 mg of meperidine administered by slow push and infused over about 5 minutes);
(ii) administering a second dose of the anti-thermoregulatory response agent to the patient (for example, about 15 minutes after the initial administration of meperidine, an additional 50 mg of meperidine is administered by slow IV push);
(iii) administering a third dose of the anti-thermoregulatory response agent by constant IV administration (for example, constant IV administration of about 25 mg/hr of meperidine maintained for the duration of the time that the patient's temperature is below the shivering threshold);
(iv) an intravenous temperature control catheter of the general type described above is introduced into the vasculature of the patient and the heat exchange region of the catheter is placed in the IVC and cooling is begun at the maximum rate. The patient is thereafter maintained at a therapeutically low temperature even below the shivering threshold.

Another class of anti-shivering drugs that may be particularly useful are the alpha-adrenergic receptor agonists, such as dexmedetomidine and clonidine.

Although several illustrative examples of means for practicing the invention are described above, these examples are by no means exhaustive of all possible means for practicing the invention. For example, the catheter device may include a plurality of gas exchange elements and/or flow disruption devices. In addition, a combination of flow disruption devices may be provided, for example, a combination of a pulsatile balloon and a plurality of ribs. Similarly, the methods of using the catheter device of the invention may be practiced in any manner in which it may be desirable to alter or maintain a patient's temperature, and/or blood gas concentration. The methods may also be useful to preserve organs in the event the organs may be used in organ transplant procedures. Other modifications to the embodiment shown in the drawings are also possible. The scope of the invention should therefore be determined with reference to the appended claims, along with the full range of equivalents to which those clams are entitled.

What is claimed is:

1. An endovascular catheter device for controlling the temperature of at least a portion of the body of a human or veterinary patient and for providing gas exchange with the patient's blood, said device comprising:

a catheter shaft that is insertable into the patient's vasculature;

a heat exchanger attached to the catheter shaft, the heat exchanger having a heat exchange surface through which heat is exchanged and with the patient's blood when the catheter shaft is inserted into the patient's vasculature;

a gas exchange element attached to the catheter shaft, the gas exchange element comprising at least one gas-permeable membrane that is separate from said heat exchanged surface are through which gas may be exchanged with the patient's blood when the catheter shaft is inserted into the patient's vasculature, a gas inflow lumen and a gas outflow lumen connected to a gas exchange device for carrying gas to and from the gas-permeable membrane;

controller apparatus connected to a temperature regulator and a gas delivery regulator for controlling the heat exchange and gas exchange being performed by the catheter device; and a blood gas concentration monitoring device connected to the controller.

2. The device of claim 1, further comprising a flow disruption device to disrupt laminarity of blood flow around the catheter device.

3. The device of claim 2, wherein the flow disruption device comprises a pulsatile element connected to the catheter shaft and disposed along the length of the shaft so that pulsations of the pulsatile element disrupt laminarity of blood around the catheter device when the device is positioned in the patient's vascular system.

4. The device of claim 2, wherein the flow disruption device is proximally disposed to the heat exchanger.

5. The device of claim 2, wherein the flow disruption device is distally disposed to the heat exchanger.

6. The device of claim 1, wherein the heat exchanger is expandable.

7. The device of claim 1, wherein the heat-exchanger comprises a heat exchange balloon.

8. The device of claim 1, wherein the heat exchanger comprises a multi-lobed heat exchange balloon.

9. The device of claim 6, wherein the lobes of the heat exchange balloon are helically arranged around the catheter shaft.

10. The device of claim 1, wherein the gas exchange element comprises a plurality of gas permeable fibers.

11. The device of claim 10, wherein the gas permeable fibers are helically arranged around the catheter shaft.

12. The device of claim 10, further comprising a pulsatile element connected to the catheter shaft and disposed between the catheter shaft and the plurality of gas permeable fibers.

13. The device of claim 12, wherein the gas exchange element is disposed proximal to the heat exchanger.

14. The device of claim 12, wherein the gas exchange element is disposed distal to the heat exchanger.

15. The device of claim 3, wherein the gas exchange element is disposed proximal to the heat exchanger, and the pulsatile element is disposed proximal to the gas exchange element.

16. A system comprising a device according to claim 1 further in combination with a temperature monitoring device connected to the controller.

17. A system according to claim 16, wherein the temperature monitoring device is in communication with the controller apparatus so that the temperature regulator adjusts the temperature of the heat exchange element based on a signal provided by the temperature monitoring device.

18. A system according to claim 1, wherein the blood gas concentration monitoring device is in communication with the controller apparatus so that the gas delivery regulator adjusts the delivery of the gas based on a signal provided by the gas concentration monitoring device.

19. A system comprising a device according to claim 1, further in combination with a cardiac monitoring device connected to the controller.

20. An endovascular catheter device, comprising:

a catheter having a proximal end, a distal end, a gas exchange inflow lumen, a gas exchange outflow lumen, a heat exchange inflow lumen and a heat exchange outflow lumen;

a heat exchanger connected to the catheter, the heat exchanger comprising a multi-lobed balloon that receives heat exchange fluid from the heat exchange inflow lumen and from which heat exchange fluid exits through the heat exchange outflow lumen; and a gas exchanger connected to the catheter, the gas exchanger comprising a plurality of gas permeable fibers that are separate from said multi-lobed balloon end which receive gas from the gas exchange inflow lumen and from which gas exits through the gas exchange outflow lumen; and a temperature probe disposed within the catheter tube so that the temperature probe can measure blood temperature of blood flowing around the catheter device when it is positioned in a patient's vascular system.

21. The device of claim 20, further comprising a flow disruption device that disrupts the flow of blood around the catheter device when the catheter device is disposed in a patient's vascular system.

22. The device of claim 21, wherein the flow disruption device is a pulsatile balloon.

23. The device of claim 22, wherein the pulsatile balloon is disposed between the catheter tube and the plurality of gas exchange fibers.

24. The device of claim 21, wherein the flow disruption device is proximally disposed to the heat exchanger.

25. The device of claim 21, wherein the flow disruption device is distally disposed to the heat exchanger.

26. The device of claim 20, wherein the gas exchanger is located proximal to the heat exchanger.

27. The device of claim 20, further comprising a gas probe disposed within the catheter tube so that the gas probe can monitor the concentration of gas in blood flowing around the catheter device when it is positioned in a patient's vascular system.

28. The device of claim 20, wherein the gas exchanger is positioned distal to the heat exchanger.

29. An endovascular catheter device for controlling the temperature of at least a portion of the body of a human or veterinary patient and for providing gas exchange with the patient's blood, said device comprising:

a catheter shaft that is insertable into the patient's vasculature;

a heat exchanger attached to the catheter shaft, the heat exchanger being constructed and positioned to exchange heat with the patient's blood when the catheter shaft is inserted into the patient's vasculature;

a gas exchange element attached to the catheter shaft, the gas exchange element comprising at least one gas-permeable membrane that is separate from said heat exchange surface are through which gas may be exchanged with the patient's blood when the catheter shaft is inserted into the patient's vasculature;

controller apparatus for controlling the heat exchange and gas exchange being performed by the catheter device; and a cardiac monitoring device connected to the controller.

30. The device of claim 29, further comprising a flow disruption device to disrupt laminarity of blood flow around the catheter device.

31. The device of claim 30, wherein the flow disruption device comprises a pulsatile element connected to the catheter shaft and disposed along the length of the shaft so that pulsations of the pulsatile element disrupt laminarity of blood around the catheter device when the device is positioned in the patient's vascular system.

32. The device of claim 30, wherein the flow disruption device is proximally disposed to the heat exchanger.

33. The device of claim 30, wherein the flow disruption device is distally disposed to the heat exchanger.

34. The device of claim 29, wherein the heat exchanger is expandable.

35. The device of claim 29, wherein the heat exchanger comprises a heat exchange balloon.

36. The device of claim 29, wherein the heat exchanger comprises a multi-lobed heat exchange balloon.

37. The device of claim 34, wherein the lobes of the heat exchange balloon are helically arranged around the catheter shaft.

38. The device of claim 29, wherein the gas exchange element comprises a plurality of gas permeable fibers.

39. The device of claim 38, wherein the gas permeable fibers are helically arranged around the catheter shaft.

40. The device of claim 38, further comprising a pulsatile element connected to the catheter shaft and disposed between the catheter shaft and the plurality of gas permeable fibers.

41. The device of claim 40, wherein the gas exchange element is disposed proximal to the heat exchanger.

42. The device of claim 40, wherein the gas exchange element is disposed distal to the heat exchanger.

43. The device of claim 31, wherein the gas exchange element is disposed proximal to the heat exchanger, and the pulsatile element is disposed proximal to the gas exchange element.

44. A device according to claim 29 wherein the catheter shaft further comprises a gas inflow lumen and a gas outflow lumen connected to a gas exchange device for carrying gas to and from the semi-permeable membrane.

45. The device of claim 44, further comprising controller apparatus connected to a temperature regulator and a gas delivery regulator for controlling the heat exchange and gas exchange being performed by the catheter device.

46. A system comprising a device according to claim 45 further in combination with a temperature monitoring device connected to the controller.

47. A system according to claim 46, wherein the temperature monitoring device is in communication with the controller apparatus so that the temperature regulator adjusts the temperature of the heat exchange element based on a signal provided by the temperature monitoring device.

48. A system comprising a device according to claim 45, further in combination with a blood gas concentration monitoring device connected to the controller.

49. A system according to claim 48, wherein the blood gas concentration monitoring device is in communication with the controller apparatus so that the gas delivery regulator adjusts the delivery of the gas based on a signal provided by the gas concentration monitoring device.

50. An endovascular catheter device, comprising:
a catheter having a proximal end, a distal end, a gas exchange inflow lumen, a gas exchange outflow lumen, a heat exchange inflow lumen and a heat exchange outflow lumen;
a heat exchanger connected to the catheter, the heat exchanger comprising a multi-lobed balloon that receives heat exchange fluid from the heat exchange inflow lumen and from which heat exchange fluid exits through the heat exchange outflow lumen;
a gas exchanger connected to the catheter, the gas exchanger comprising a plurality of gas permeable fibers that are separate from said multi-lobed balloon and which receive gas from the gas exchange inflow lumen and from which gas exits through the gas exchange outflow lumen; and
a gas probe disposed within the catheter tube so that the gas probe can monitor the concentration of gas in blood flowing around the catheter device when it is positioned in a patient's vascular system.

51. The device of claim 50, further comprising a flow disruption device that disrupts the flow of blood around the catheter device when the catheter device is disposed in a patient's vascular system.

52. The device of claim 51, wherein the flow disruption device is a pulsatile balloon.

53. The device of claim 52, wherein the pulsatile balloon is disposed between the catheter tube and the plurality of gas exchange fibers.

54. The device of claim 51, wherein the flow disruption device is proximally disposed to the heat exchanger.

55. The device of claim 51, wherein the flow disruption device is distally disposed to the heat exchanger.

56. The device of claim 50, wherein the gas exchanger is located proximal to the heat exchanger.

57. The device of claim 50, further comprising a temperature probe disposed within the catheter tube so that the temperature probe can measure blood temperature of blood flowing around the catheter device when it is positioned in a patient's vascular system.

58. The device of claim 50, wherein the gas exchanger is positioned distal to the heat exchanger.

59. A method of controlling the temperature of at least a portion of the body of a human or veterinary patient and for controlling the concentration of oxygen in the patient's blood, the method comprises the steps of:
(a) inserting a catheter device into the patient's vasculature, the catheter device comprising a catheter having a first inflow lumen, a first outflow lumen, a second inflow lumen and a second outflow lumen, a gas exchanger and a heat exchanger;
(b) delivering a heat exchange fluid through the heat exchanger via the first inflow lumen, the heat exchange fluid having being of a temperature that results in heat being exchanged between the heat exchange fluid and the patient's blood, through the heat exchanger; and
(c) delivering a gaseous substance through the gas exchanger via the second inflow lumen so that the gas is exchanged between the gaseous substance and the patient's blood, through the gas exchanger.

60. The method of claim 59, further comprising a step of:
(d) disrupting a laminar flow of blood around the catheter device to enhance temperature and gas exchange between the catheter device and the patient's blood.

61. The method of claim 60, wherein the catheter inserted in Step (a) further comprises a pulsating balloon and wherein Step (d) comprises disrupting the laminar flow of blood by causing pulsation of the pulsating balloon.

62. The method of claim 59, wherein the heat exchange fluid is cooler than the patient's blood and thereby causes a decrease in the patient's temperature.

63. The method of claim 59, wherein the gas is oxygen.

64. The method of claim 59, wherein the gas is an anesthetic.

65. The method of claim 59, wherein the patient has suffered from a myocardial infarction.

66. The method of claim 59, wherein the patient has suffered from a stroke.

67. The method of claim 59, further comprising a step of monitoring the patient's temperature and blood gas concentration.

68. The method of claim 67, wherein the patient's temperature and blood gas concentration are monitored by at least one probe disposed within the catheter device.

69. The method of claim 67, further comprising a step of adjusting the temperature of the heat exchanger based on the patient's temperature so monitored.

70. The method of claim 69, wherein the temperature of the heat exchanger is adjusted by changing the temperature of the fluid flowing through the heat exchanger.

71. The method of claim 69, wherein the temperature of the heat exchanger is adjusted by changing the flow rate of the fluid flowing through the heat exchanger.

72. The method of claim 67, further comprising a step of adjusting the gas exchange rate of the gas exchanger based on the patient's blood gas concentration so monitored.

73. The method of claim 72, wherein the gas exchange rate is adjusted by adjusting the flow rate of the gas through the gas exchanger.

74. The method of claim 72, wherein the gas exchange rate is adjusted by adjusting the gas concentration of the gas flowing through the gas exchanger.

75. The method of claim 59, wherein the catheter device is inserted in the vascular system in proximity to the patient's heart.

76. The method of claim 59, further comprising a step of reducing shivering of the patient.

77. The method of claim 76, wherein the step of reducing shivering comprises administering an anti-shivering mechanism to the patient.

78. The method of claim 77, wherein the anti-shivering mechanism is a blanket.

79. The method of claim 77, wherein the anti-shivering mechanism is a pharmaceutical.

\* \* \* \* \*